(12) United States Patent
Nuvoli et al.

(10) Patent No.: US 10,427,234 B2
(45) Date of Patent: Oct. 1, 2019

(54) METHOD FOR BRAZING A METAL PART ONTO A ZIRCONIA COMPONENT, AND BRAZED IMPLANTABLE DEVICE

(71) Applicant: PNL HOLDING, Collegien (FR)

(72) Inventors: Didier Nuvoli, Choisy le Roi (FR); Yvan Paquin, Iverny (FR)

(73) Assignee: PNL HOLDING, Collegien (FR)

( * ) Notice: Subject to any disclaimer, the term of this patent is extended or adjusted under 35 U.S.C. 154(b) by 350 days.

(21) Appl. No.: 15/586,484

(22) Filed: May 4, 2017

(65) Prior Publication Data

US 2017/0326664 A1 Nov. 16, 2017

(30) Foreign Application Priority Data

May 11, 2016 (FR) ...................... 16 54208

(51) Int. Cl.
| | |
|---|---|
| *B23K 1/19* | (2006.01) |
| *A61N 1/05* | (2006.01) |
| *A61N 1/375* | (2006.01) |
| *B23K 1/00* | (2006.01) |
| *B23K 31/12* | (2006.01) |
| *B23K 35/30* | (2006.01) |
| *C22F 1/18* | (2006.01) |
| *B23K 1/20* | (2006.01) |
| *B23K 101/30* | (2006.01) |

(Continued)

(52) U.S. Cl.
CPC ................ *B23K 1/19* (2013.01); *A61N 1/375* (2013.01); *B23K 1/0008* (2013.01); *B23K 1/20* (2013.01); *B23K 1/206* (2013.01); *B23K 31/125* (2013.01); *B23K 35/3013* (2013.01); *C22F 1/183* (2013.01); *B23K 2101/30* (2018.08); *B23K 2101/34* (2018.08); *B23K 2103/14* (2018.08); *B23K 2103/172* (2018.08); *B23K 2103/52* (2018.08)

(58) Field of Classification Search
CPC ............................... A61N 1/375; C22F 1/183
See application file for complete search history.

(56) References Cited

U.S. PATENT DOCUMENTS

| | | | |
|---|---|---|---|
| 4,225,262 A | 9/1980 | Koop et al. | |
| 2005/0194690 A1 | 9/2005 | Ishii et al. | |
| 2015/0165218 A1* | 6/2015 | Markham | ............ A61N 1/3754 607/116 |

FOREIGN PATENT DOCUMENTS

EP  1 542 271 A1  6/2005

OTHER PUBLICATIONS

French Preliminary Search Report for corresponding FR 16 54208, dated Jul. 27, 2016.

* cited by examiner

*Primary Examiner* — Lois L Zheng
(74) *Attorney, Agent, or Firm* — Sughrue Mion, PLLC

(57) ABSTRACT

A method for brazing a metal part onto a surface of a zirconia component. The method involves the steps of altering the surface state of the component to permit the attachment of a first metallization layer, cleaning the component to eliminate the impurities from its surface, depositing a first metallization layer, having mainly titanium, on the surface of the component, depositing a second metallization layer, having mainly niobium, on the first metallization layer, applying the part against the second metallization layer, depositing a gold brazing metal on the part and the second metallization layer, cooling the brazed area in a temperature-controlled manner, and stress-relieving heat treatment being performed under load on the metal part before brazing.

15 Claims, 2 Drawing Sheets

(51) Int. Cl.
*B23K 101/34* (2006.01)
*B23K 103/14* (2006.01)
*B23K 103/00* (2006.01)
*B23K 103/16* (2006.01)

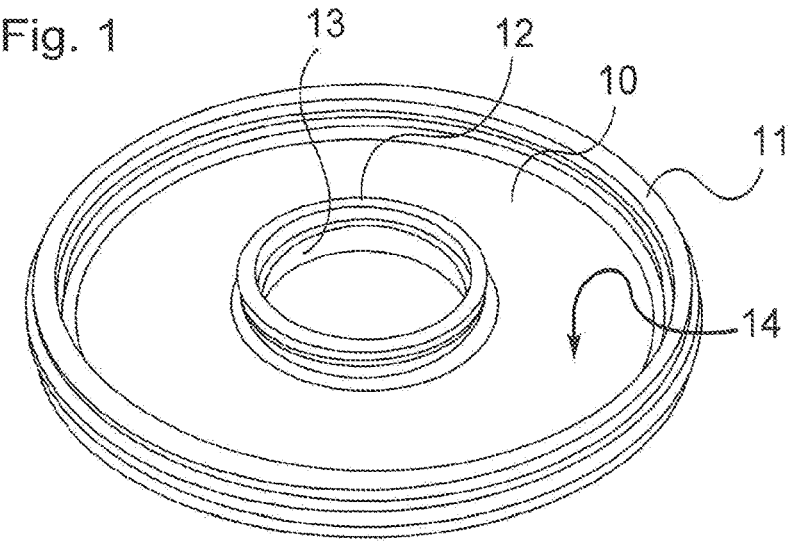
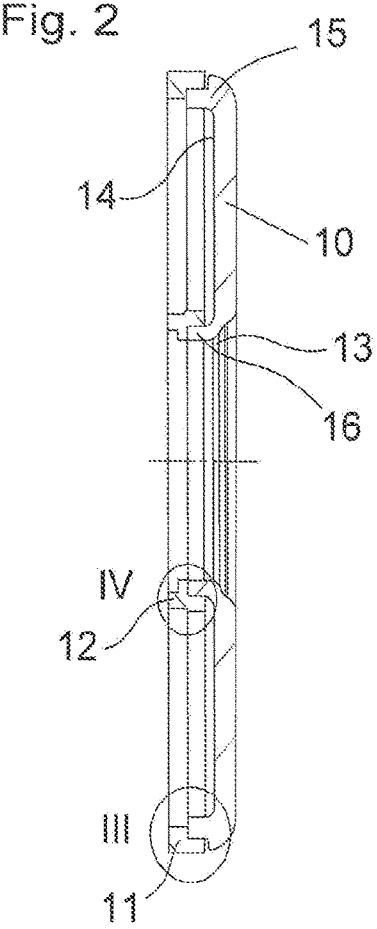
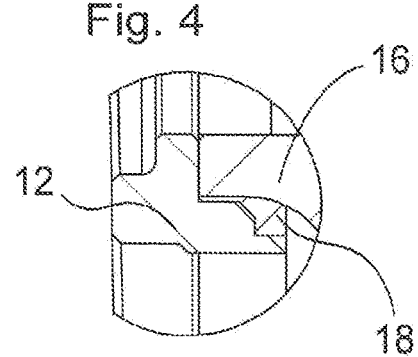
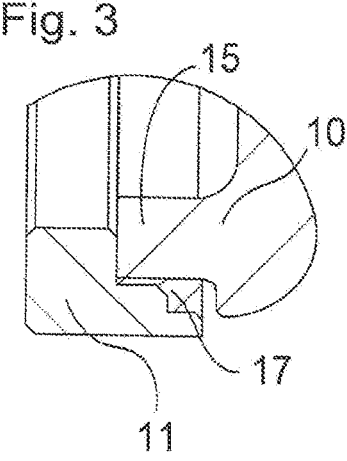

METHOD FOR BRAZING A METAL PART ONTO A ZIRCONIA COMPONENT, AND BRAZED IMPLANTABLE DEVICE

The present invention relates to the field of brazing metal parts onto ceramics.

PRIOR ART

There are known devices which are implantable into the human body, such as cardiac pacemakers or cochlear implants, which comprise a probe connected to an electronic circuit enclosed in a ceramic housing. The ceramic that is used is generally made of alumina.

The standards applicable to devices implantable into the human body currently specify that the housing must withstand impacts of 2.5 joules.

To meet these standards, it has been proposed that a stronger ceramic should be used, more particularly a zirconium dioxide, or zirconia, ceramic. However, it has been found that the manufacture of zirconia housings gives rise to problems. In particular, the conventional manufacture of alumina housings includes brazing operations which cannot be carried out on zirconia. This solution has not been developed further.

This problem of brazing a metal part onto a zirconia component also arises in fields other than that of devices implantable into the human body.

OBJECT OF THE INVENTION

One object of the invention is to provide a means for brazing a metal part onto a zirconia component.

BRIEF DESCRIPTION OF THE INVENTION

For this purpose, a method is provided, according to the invention, for brazing a metal part onto a surface of a zirconia component, comprising the steps of:
  altering the surface state of the component to permit the attachment of a first metallization layer,
  cleaning the component to eliminate impurities from its surface,
  depositing the first metallization layer, consisting mainly of titanium, on the surface of the component,
  depositing a second metallization layer, consisting mainly of niobium, on the first metallization layer,
  applying the part against the second metallization layer,
  depositing a gold brazing metal on the part and the second metallization layer, and
  cooling the brazed area in a temperature-controlled manner,
  stress-relieving heat treatment being performed under load on the metal part before brazing.

The alteration of the surface state enables its roughness to be increased to promote the attachment of the first metallization layer. The first metallization layer permits the attachment of the second metallization layer. The second metallization layer permits the attachment of the gold brazing metal, which adheres to the metal part. Stress relieving under load makes it possible to eliminate the stresses accumulated in the metal part during its manufacture, while avoiding the deformation of the metal part. These stresses, if not eliminated in advance, could cause cracks in the brazed area when this is cooled.

Other characteristics and advantages of the invention will be evident from the following description of non-limiting specific embodiments of the invention.

BRIEF DESCRIPTION OF THE DRAWINGS

Reference will be made to the attached drawings, in which:
FIG. 1 is a partial perspective view of a housing according to a first embodiment of the invention;
FIG. 2 is a sectional view of a variant of the first embodiment of the invention;
FIGS. 3 and 4 are detail views of areas III and IV of FIG. 2.

DETAILED DESCRIPTION OF THE INVENTION

Figure 5:
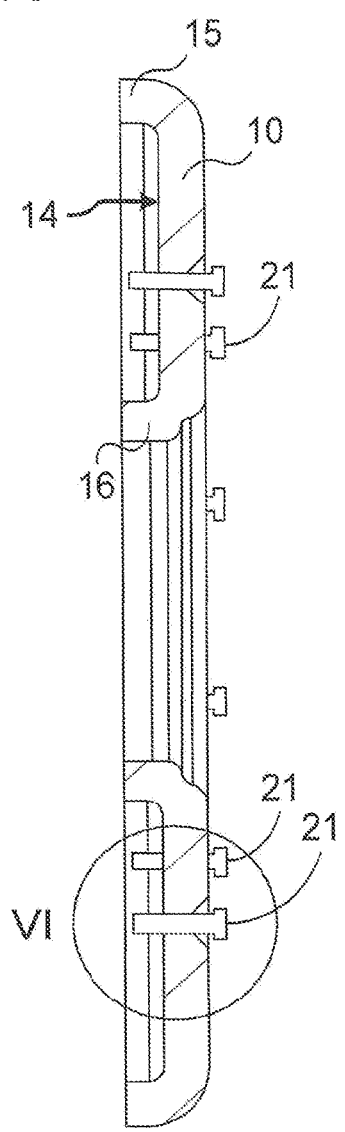
FIG. 5 is a partial perspective view of a housing according to a second embodiment of the invention.

The invention is described here in its application to the manufacture of a housing for a device which is implantable into the human body. Evidently, the invention may be used for the manufacture of other products comprising a zirconia part to which a metal part is to be fixed.

With reference to the figures, the device of the invention comprises a housing having a plate 10 made of zirconia, in this case a Type C5 yttria-stabilized zirconia. In this case, the plate 10 is circular in shape.

At least one metal part is fixed to the zirconia plate by brazing.

With reference to FIG. 1, and according to the first embodiment, two metal parts 11, 12 are fixed to the plate 10. The metal part 11 is a circular collar fixed to the outer circumference of the plate 10. The metal part 12 is a circular collar fixed to the periphery of a hole 13 formed in the center of the plate 10. Both of the metal parts 11, 12 extend in a projecting manner from the same surface 14 of the plate 10, and form a closed contour.

The metal parts 11 and 12 are both made of titanium.

The brazing metal which joins the plate 10 to each of the metal parts 11, 12 is continuous, and provides a fluid-tight joint between each of the metal parts 11, 12 and the plate 10.

With reference to FIGS. 2 to 4, and according to the variant of the first embodiment, the plate 10 comprises an outer annular rim 15 extending in a projecting manner from the surface 14, from the outer edge of the plate 10, and an inner annular rim 16 extending in a projecting manner from the surface 14 around the hole 13.

The metal part 11 is a circular collar, an annular rim 17 of which is engaged around the outer annular rim 15 of the plate 10. The metal part 12 is a circular collar, an annular rim 18 of which is engaged within the inner annular rim 16 of the plate 10.

As before, the brazing metal which joins the plate 10 to each of the metal parts 11, 12 is continuous, and provides a fluid-tight joint between each of the metal parts 11, 12 and the plate 10.

Figure 6:
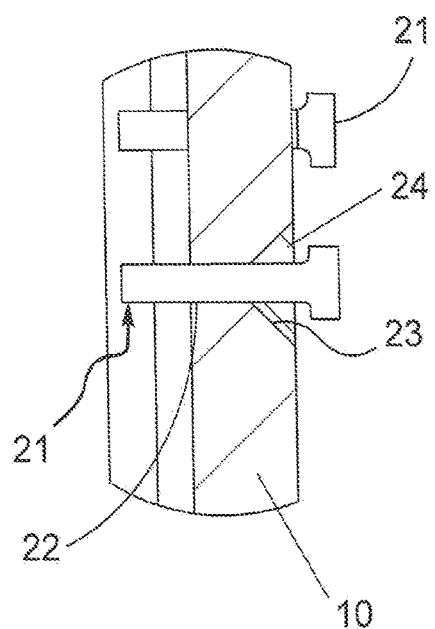
FIG. 6 is a detail view of area VI of FIG. 5.

With reference to FIGS. 5 and 6, and according to the second embodiment, the shape of the plate 10 is substantially identical to that of the plate 10 of FIG. 2.

Metal parts 21, forming electrical conduction pins, pass through the plate 10 in the annular area extending between the collars 15 and 16. More precisely, the metal parts 21 each have a central portion received in a bore 22 which is formed in said area of the plate 10, and which opens with a chamfer 23 onto a surface of the plate 10 opposite the surface 14. A brazing metal 24 extends in the chamfer 23 and between the wall of the bore 22 and the outer surface of each conductive element 21. The brazing metal 24 extends continuously along the periphery of each bore 22 and of the corresponding metal part 21, to ensure the fluid-tightness of the passage of the metal parts 21.

In this case, the material of the metal parts 21 is an alloy of platinum and iridium.

The brazing of the metal parts 11, 12, 21 onto the plates 10 is carried out by the brazing method according to the invention.

This brazing method will now be described.

According to the invention, the brazing method starts with preparatory steps which have the aim of promoting the subsequent attachment of the brazing metal to the plate 10.

Thus, sandblasting is performed, with the aim of altering the surface state of the plate to increase its roughness and permit the attachment of a first metallization layer. The sandblasting is carried out on the surface intended to receive the first metallization layer.

The desired roughness is approximately 0.4 µm.

The plate is then treated to eliminate the impurities from its surface.

This treatment comprises:
an acetone cleaning operation, followed by
a burning operation performed at a temperature of approximately 1000° C.

This cleans the surface of the plate and removes the organic impurities from it.

The first metallization layer is then deposited on the surface of the plate 10 which will be in contact with the brazing metal. The first metallization layer consists mainly of titanium. More precisely, in this case the first metallization layer comprises approximately 100% titanium. The thickness of the first metallization layer is in the range from approximately 4 to 8 µm.

A second metallization layer is then deposited on the first metallization layer. The second metallization layer consists mainly of niobium. More precisely, in this case the second metallization layer comprises approximately 100% niobium. The thickness of the second metallization layer is in the range from approximately 4 to 8 µm.

Simultaneously with the preparatory steps performed on the plate, a stress-relieving heat treatment is performed under load on the metal part.

This enables the stresses due to machining to be released without causing deformation of the metal part.

The brazing may then be carried out.

Initially, the metal part is applied against the second metallization layer, after which the molten gold brazing metal is deposited on the part and the second metallization layer.

The brazed area is then cooled in a temperature-controlled manner. The aim of the control method is to carry out rapid cooling to 900° C., followed by cooling at 3° C. per minute to 250° C. Cooling is then natural until ambient temperature is reached.

A set of tests is then conducted to ensure the quality of the weld.

Thus the method comprises:
a step of checking the fluid-tightness of the brazing metal, and
a step of subjecting the brazed assembly to thermal shock and a step of checking the fluid-tightness of the brazing metal. The thermal shocks are executed between a lower temperature of approximately −55° C. and an upper temperature of approximately +150° C.

The method of the invention is executed by using a furnace providing uniform heat distribution so as to provide a heat dispersion of 2° C. or less on the surface of the plate.

Clearly, the invention is not limited to the embodiments described above, but incorporates all variants falling within the scope of the invention as defined by the claims.

In particular, the invention may be used with other zirconias, and with metals other than those mentioned.

The stress-relieving heat treatment could be carried out after the part has been applied against the second metallization layer.

It is also possible to conduct burn-in and ageing tests.

The invention claimed is:

1. A method for brazing a metal part onto a surface of a zirconia component, comprising the steps of:
    altering the surface state of the component to permit attachment of a first metallization layer,
    cleaning the component to eliminate impurities from its surface,
    depositing a first metallization layer, consisting mainly of titanium, on the surface of the component,
    depositing a second metallization layer, consisting mainly of niobium, on the first metallization layer,
    applying the part against the second metallization layer,
    depositing a gold brazing metal on the part and the second metallization layer, and
    cooling the brazed area in a temperature-controlled manner,
    stress-relieving heat treatment being performed under load on the metal part before brazing.

2. The method as claimed in claim 1, wherein the alteration of surface state comprises sandblasting.

3. The method as claimed in claim 2, wherein the surface after alteration has a roughness of approximately 0.4 µm.

4. The method as claimed in claim 1, wherein the cleaning step comprises a burning operation.

5. The method as claimed in claim 4, wherein the burning is carried out at a temperature of approximately 1000°.

6. The method as claimed in claim 1, wherein the first metallization layer comprises approximately 100% titanium.

7. The method as claimed in claim 1, wherein the second metallization layer comprises approximately 100% niobium.

8. The method as claimed in claim 1, wherein the part is made of titanium.

9. The method as claimed in claim 1, wherein the part comprises platinum and iridium.

10. The method as claimed in claim 1, wherein the component is a plate and the part has a closed contour, the brazing metal being continuous along the part and the component, the method comprising a further step of checking the fluid-tightness of the brazing metal.

11. The method as claimed in claim 10, wherein the plate comprises an annular rim to be fixed to the part by the brazing metal.

12. The method as claimed in claim 10, further comprising a step of subjecting the brazed assembly to thermal shock and a step of checking the fluid-tightness of the brazing metal.

13. The method as claimed in claim 12, wherein the thermal shocks are executed between a lower temperature of approximately −55° C. and an upper temperature of approximately +150° C.

14. The method as claimed in claim 1, wherein the stress-relieving heat treatment, being performed under load on the metal part before brazing, is carried out before the part is applied against the second metallization layer.

15. Device implantable into the human body, comprising a housing including a plate of zirconia onto which a titanium collar is brazed by the method as claimed in claim 1.

* * * * *